US006475435B1

(12) United States Patent
Taggart

(10) Patent No.: US 6,475,435 B1
(45) Date of Patent: Nov. 5, 2002

(54) APPARATUS AND METHOD FOR PROVIDING STERILIZATION ZONES IN AN ASEPTIC PACKAGING STERILIZATION TUNNEL

(75) Inventor: Thomas D. Taggart, South Wales, NY (US)

(73) Assignee: Steuben Foods Incorporated, Elma, NY (US)

( * ) Notice: Subject to any disclaimer, the term of this patent is extended or adjusted under 35 U.S.C. 154(b) by 0 days.

(21) Appl. No.: 09/330,763

(22) Filed: Jun. 11, 1999

Related U.S. Application Data

(60) Provisional application No. 60/118,404, filed on Feb. 2, 1999.

(51) Int. Cl.[7] .............................. A61L 2/00; A61L 9/00; A01N 1/00; B65B 55/00; B65B 55/02

(52) U.S. Cl. ............................ 422/33; 422/28; 422/295; 422/302; 422/304; 53/167; 53/168; 53/425; 53/426

(58) Field of Search .......................... 53/167, 425, 426, 53/453, 28, 33; 422/302, 304

(56) References Cited

U.S. PATENT DOCUMENTS

| | | | | | |
|---|---|---|---|---|---|
| 2,380,984 | A | | 8/1945 | Moeller | 226/68 |
| 3,783,581 | A | | 1/1974 | Pierce | 53/37 |
| 3,891,779 | A | | 6/1975 | Robinson | 426/399 |
| 3,899,862 | A | * | 8/1975 | Muys et al. | 53/162 |
| 4,045,945 | A | | 9/1977 | Moller et al. | 53/167 |
| 4,175,140 | A | | 11/1979 | Bachmann et al. | 426/399 |
| 4,296,068 | A | * | 10/1981 | Hoshino | 422/304 |
| 4,369,898 | A | | 1/1983 | Andersson | 222/4 |
| 4,494,357 | A | | 1/1985 | DiGeronimo | 53/167 |
| 4,566,591 | A | | 1/1986 | Turtschan et al. | 206/427 |
| 4,597,242 | A | | 7/1986 | Hendriks et al. | 53/426 |
| 4,622,800 | A | | 11/1986 | Turtschan | 53/425 |
| 4,730,482 | A | | 3/1988 | Cerny et al. | 73/49.3 |
| 4,903,891 | A | | 2/1990 | Gordon | 229/48 |
| 4,936,486 | A | | 6/1990 | Kummerer | 222/42 |
| 4,987,721 | A | | 1/1991 | Turtschan | 53/67 |
| 4,987,726 | A | | 1/1991 | Petho et al. | 53/510 |
| 4,992,247 | A | | 2/1991 | Foti | 422/304 |
| 4,996,824 | A | | 3/1991 | Torterotot | 53/426 |
| 5,001,886 | A | | 3/1991 | Turtschan | 53/167 |
| 5,007,232 | A | | 4/1991 | Caudill | 53/426 |
| 5,251,423 | A | | 10/1993 | Turtschan | 53/426 |
| 5,313,990 | A | | 5/1994 | Clusserath | 141/6 |
| 5,365,774 | A | | 11/1994 | Horlacher | 73/43.9 |
| 5,398,734 | A | | 3/1995 | Hartel | 141/82 |
| 5,406,772 | A | | 4/1995 | Dinius | 53/67 |
| 5,529,099 | A | | 6/1996 | Janek et al. | 141/129 |
| 5,534,222 | A | * | 7/1996 | Kelbrick et al. | 422/33 |
| 5,564,481 | A | | 10/1996 | Clusserath | 141/92 |
| 5,673,535 | A | | 10/1997 | Jagger | 53/282 |
| 5,720,148 | A | | 2/1998 | Bedin et al. | 53/167 |
| 5,848,515 | A | | 12/1998 | Catelli et al. | 53/167 |

FOREIGN PATENT DOCUMENTS

| | | |
|---|---|---|
| EP | 0 569 754 B1 | 5/1998 |
| KR | 96-8699 | 6/1996 |

OTHER PUBLICATIONS

Bosch Product Literature: "Aseptically operating filling and closing lines for bottles, jars and wide–mouth containers of glass".

* cited by examiner

*Primary Examiner*—Robert J. Warden, Sr.
*Assistant Examiner*—Imad Soubra
(74) *Attorney, Agent, or Firm*—Schmeiser, Olsen & Watts

(57) ABSTRACT

A method and apparatus is disclosed providing a plurality of sterile zones within a sterilization tunnel in an aseptic packaging apparatus. The sterile zones provide a plurality of sterilant concentration levels within the sterilization tunnel. Additionally, the sterile zones provide a plurality of gas flow rates within the sterilization tunnel.

37 Claims, 14 Drawing Sheets

APPARATUS AND METHOD FOR PROVIDING STERILIZATION ZONES IN AN ASEPTIC PACKAGING STERILIZATION TUNNEL

This application claims the benefit of provisional application No. 60/118,404 filed Feb. 2, 1999.

FIELD OF THE INVENTION

The present invention relates generally to systems for the aseptic packaging of food products. More particularly, the present invention relates to an apparatus and method for providing sterilization zones in an aseptic packaging sterilization tunnel.

BACKGROUND OF THE INVENTION

Sterilized packaging systems in which a sterile food product is placed and sealed in a container to preserve the product for later use are well known in the art. Methods of sterilizing incoming containers, filling the containers with pasteurized product, and sealing the containers in an aseptic tunnel are also known.

Packaged food products can generally be categorized as high acid products (Ph below 4.5) or low acid products (Ph of 4.5 and above). The high acid content of a high acid product helps to reduce bacteria growth in the product, thereby increasing the shelf life of the product. The low acid content of a low acid product, however, necessitates the use of more stringent packaging techniques, and often requires refrigeration of the product at the point of sale.

Several packaging techniques, including extended shelf life (ESL) and aseptic packaging, have been developed to increase the shelf life of low acid products. During ESL packaging, for example, the packaging material is commonly sanitized and filled with a product in a presterilized tunnel under "ultra-clean" conditions. By using such ESL packaging techniques, the shelf life of an ESL packaged product is commonly extended from about 10 to 15 days to about 90 days. Aseptic packaging techniques, however, which require that the packaging take place in a sterile environment, using presterilized containers, etc., are capable of providing a packaged product having an even longer shelf life of 150 days or more. In fact, with aseptic packaging, the shelf life limitation is often determined by the quality of the taste of the packaged product, rather than by a limitation caused by bacterial growth.

For the aseptic packaging of food products, an aseptic filler must, for example, use an FDA (Food and Drug Administration) approved sterilant, meet FDA quality control standards, use a sterile tunnel or clean room, and must aseptically treat all packaging material. The food product must also be processed using an "Ultra High Temperature" (UHT) pasteurization process to meet FDA aseptic standards. The packaging material must remain in a sterile environment during filling, closure, and sealing operations.

Many attempts have been made, albeit unsuccessfully, to aseptically fill containers, such as bottles or jars having small openings, at a high output processing speed. In addition, previous attempts for aseptically packaging a low acid product in plastic bottles or jars (e.g., formed of polyethylene terepthalate (PET) or high density polyethylene (HDPE)), at a high output processing speed, have also failed. Furthermore, the prior art has not been successful in providing a high output aseptic filler that complies with the stringent United States FDA standards for labeling a packaged product as "aseptic." In the following description of the present invention, the term "aseptic" denotes the United States FDA level of aseptic.

SUMMARY OF THE INVENTION

In order to overcome the above deficiencies, the present invention provides a method and apparatus for providing aseptically processed low acid products in a container having a small opening, such as a glass or plastic bottle or jar, at a high output processing speed.

Many features are incorporated into the aseptic processing apparatus of the present invention in order to meet the various FDA aseptic standards and the 3A Sanitary Standards and Accepted Practices.

The aseptic processing apparatus of the present invention uses a gas such as filtered air to maintain a positive pressure within a filler apparatus. The filler apparatus includes a sterilization tunnel that is pressurized to a level greater than atmospheric pressure using filtered sterile air. The filler apparatus includes three interfaces with the ambient environment, each of which eliminates the possibility of external contamination. The first interface is where containers first enter the sterilization tunnel through a bottle infeed and sterilization apparatus. In accordance with the present invention, there is always an outflow of aseptic sterilant (e.g., hydrogen peroxide) enriched sterile air from the first interface to prevent contaminants from entering the sterilization tunnel. The second interface with the sterilization tunnel is the path where incoming lid stock enters a lid sealing and heat sealing apparatus. To prevent contamination, the lid stock passes through a hydrogen peroxide bath that provides an aseptic barrier for any contaminants that enter the sterilization tunnel through the second interface. The third interface with the sterilization tunnel is at an exit opening of a discharge apparatus where sealed containers leave the sterilization tunnel. Positive sterile air pressure within the sterilization tunnel ensures that sterile air is continuously flowing out of the exit opening of the discharge apparatus, thereby preventing contaminants from entering the sterilization tunnel through this interface.

The aseptic processing apparatus includes a conveying apparatus for transporting the containers through a plurality of processing stations located within the sterilization tunnel. The entire conveying apparatus is enclosed within the sterilization tunnel, and is never is exposed to unsterile conditions.

A plurality of partitions and a plurality of hot sterile air supply sources (e.g., conduits) provide a plurality of sterile zones within the sterilization tunnel. The sterile zones provide a plurality of sterilant concentration levels withing the sterilization tunnel. Additionally, the sterile zones provide a plurality of gas flow rates within the sterilization tunnel.

The interior surface of a container such as a bottle or jar is much more difficult to aseptically sterilize than the interior surface of a cup. A cup generally has a large opening compared to its height, whereas a bottle or jar generally has a small opening compared to its height and its greatest width (e.g., the ratio of the opening diameter to the height of the container is less than 1.0). A sterilant can be introduced, activated, and removed in a cup much more rapidly than in a bottle or jar. The processing speed when using a bottle or jar is limited, in part, by the time required to aseptically sterilize the interior surface of the bottle or jar. The aseptic processing apparatus of the present invention overcomes the processing speed limitations associated with the use of containers such as bottles or jars.

A high output processing speed is achieved in the present invention by applying a hot atomized sterilant, such as hydrogen peroxide spray onto the interior surface of each container, and by subsequently activating and removing the sterilant in a plurality of drying stations using hot sterile air. For example hydrogen peroxide breaks down into water and oxygen, and thus oxidizes and kills bacteria within the container. To achieve aseptic sterilization, a minimum container temperature is developed and held for a predetermined period of time (e.g., 131° F. for 5 seconds) after application of the sterilant. Hot sterile air is delivered at a high volume and a relatively low temperature to dry the container and to prevent the container (if formed of plastic) from being heated to its softening temperature. After container drying, the residual hydrogen peroxide in the container is below a predetermined level (e.g., about 0.5 PPM (parts per million)).

The present invention generally provides an apparatus comprising:

a sterilization tunnel for surrounding a plurality of containers with pressurized gas; and a plurality of zones within a sterilization tunnel having different sterilant concentration levels.

Also provided is a method comprising:

providing a sterilization tunnel for surrounding a plurality of containers with pressurized gas;

introducing sterilant from a sterilant supply source into the sterilization tunnel;

providing a plurality of sterilant concentration zones within the sterilization tunnel;

introducing pressurized gas from at least one gas supply source into the sterilization tunnel; and allowing the pressurized gas to escape the sterilization tunnel.

The invention further provides an apparatus comprising:

means for providing a plurality of containers in a sterilization tunnel;

means for providing a plurality of sterilant concentration zones within the sterilization tunnel; and means for providing a plurality of gas flow rates within the sterilization tunnel.

BRIEF DESCRIPTION OF THE DRAWINGS

The features of the present invention will best be understood from a detailed description of the invention and a preferred embodiment, thereof selected for the purposes of illustration, and shown in the accompanying drawings in which.

DETAILED DESCRIPTION OF THE INVENTION

Figure 1:
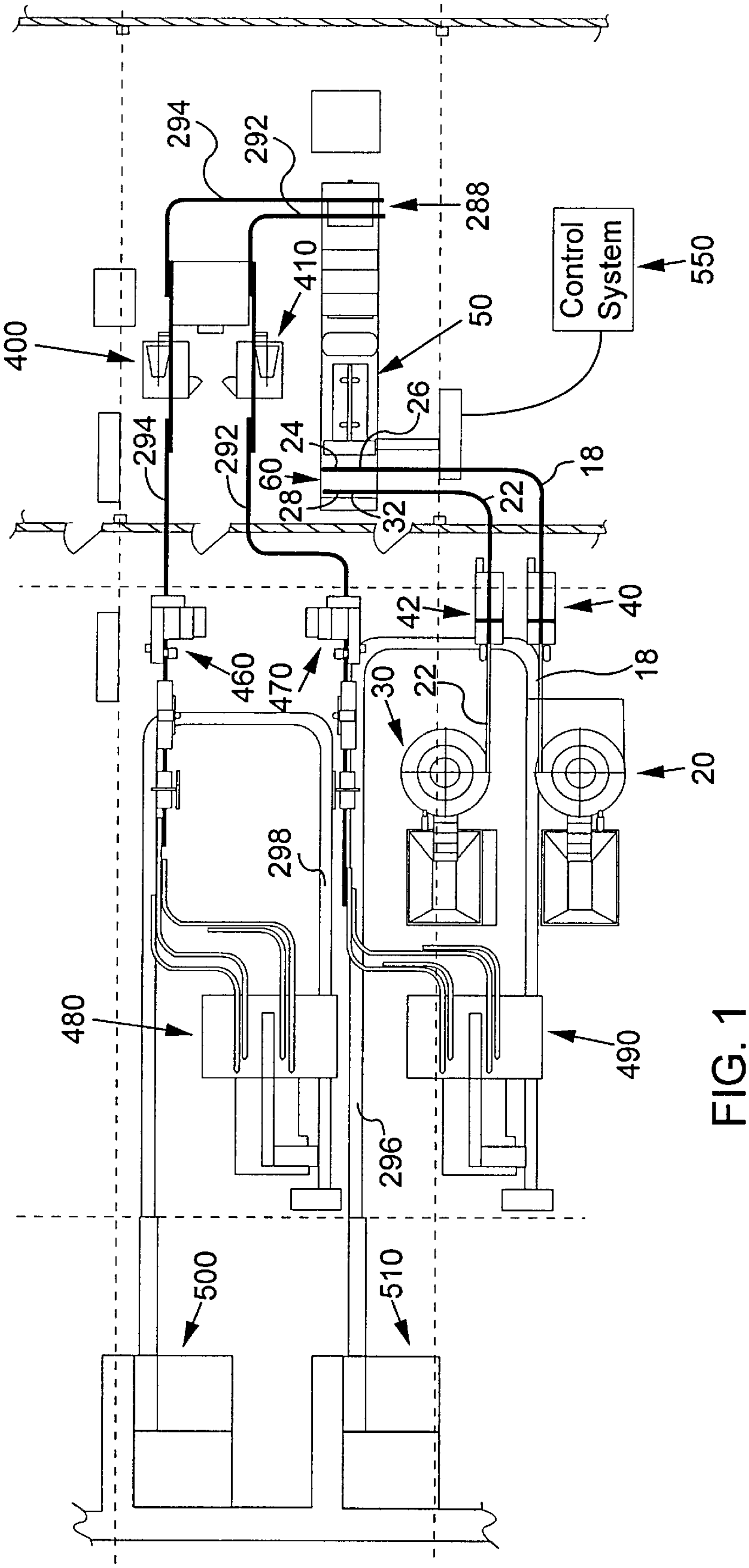
FIG. 1 is a plain view of an aseptic processing apparatus in accordance with a preferred embodiment of the present invention.

Although certain preferred embodiments of the present invention will be shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of the preferred embodiment. The features and advantages of the present invention are illustrated in detail in the accompanying drawings, wherein like reference numerals refer to like elements throughout the drawings. Although the drawings are intended to illustrate the present invention, the drawings are not necessarily drawn to scale.

The present invention provides an aseptic processing apparatus 10 that will meet the stringent United States FDA (Food and Drug Administration) requirements and 3A Sanitary Standards and Accepted Practices required to label a food product (foodstuffs) as "aseptic". Hereafter, "aseptic" will refer to the FDA level of aseptic. The present invention provides an aseptic processing apparatus 10 for producing at least about a 12 log reduction of *Clostridium botulinum* in food products. In addition, the present invention produces packaging material with at least about a 6 log reduction of spores. Actual testing of the aseptic processing apparatus is accomplished with spore test organisms. These test organisms are selected on their resistance to the media selected used to achieve sterility. For example, when steam is the media, the test organism is *Bacillus stearothermophilus*. When hydrogen peroxide is the media, then the test organism is *Bacillus subtilis* var. globigii.

The present invention processes containers such as bottles or jars that have a small opening compared to its height and its greatest width (e.g., the ratio of the opening diameter to the height of the container is less than 1.0). In the preferred embodiment, a bottle 12 (see, e.g., FIG. 8) is illustrated as the container. The container may alternately comprise a jar. The bottle 12 is preferably formed of a plastic such as polyethylene terepthalate (PET) or high density polyethylene (HDPE), although other materials such as glass may also be used. The present invention uses an aseptic sterilant such as hydrogen peroxide ($H_2O_2$) or oxonia (hydrogen peroxide and peroxyacetic acid) to sterilize the bottles 12. In the preferred embodiment of the present invention, hydrogen peroxide is used as the sterilant. The present invention uses hydrogen peroxide with a concentration of less than about 35% and ensures that the bottles 12 have less than about 0.5 ppm of residual hydrogen peroxide after each bottle 12 is sterilized.

Figure 2:
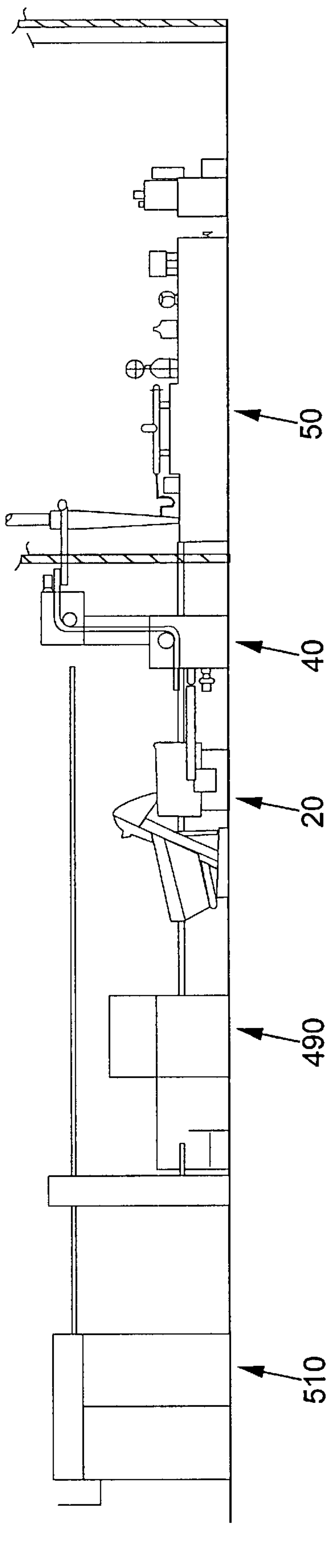
FIG. 2 is a side view of the aseptic processing apparatus of FIG. 1.
Figure 3:
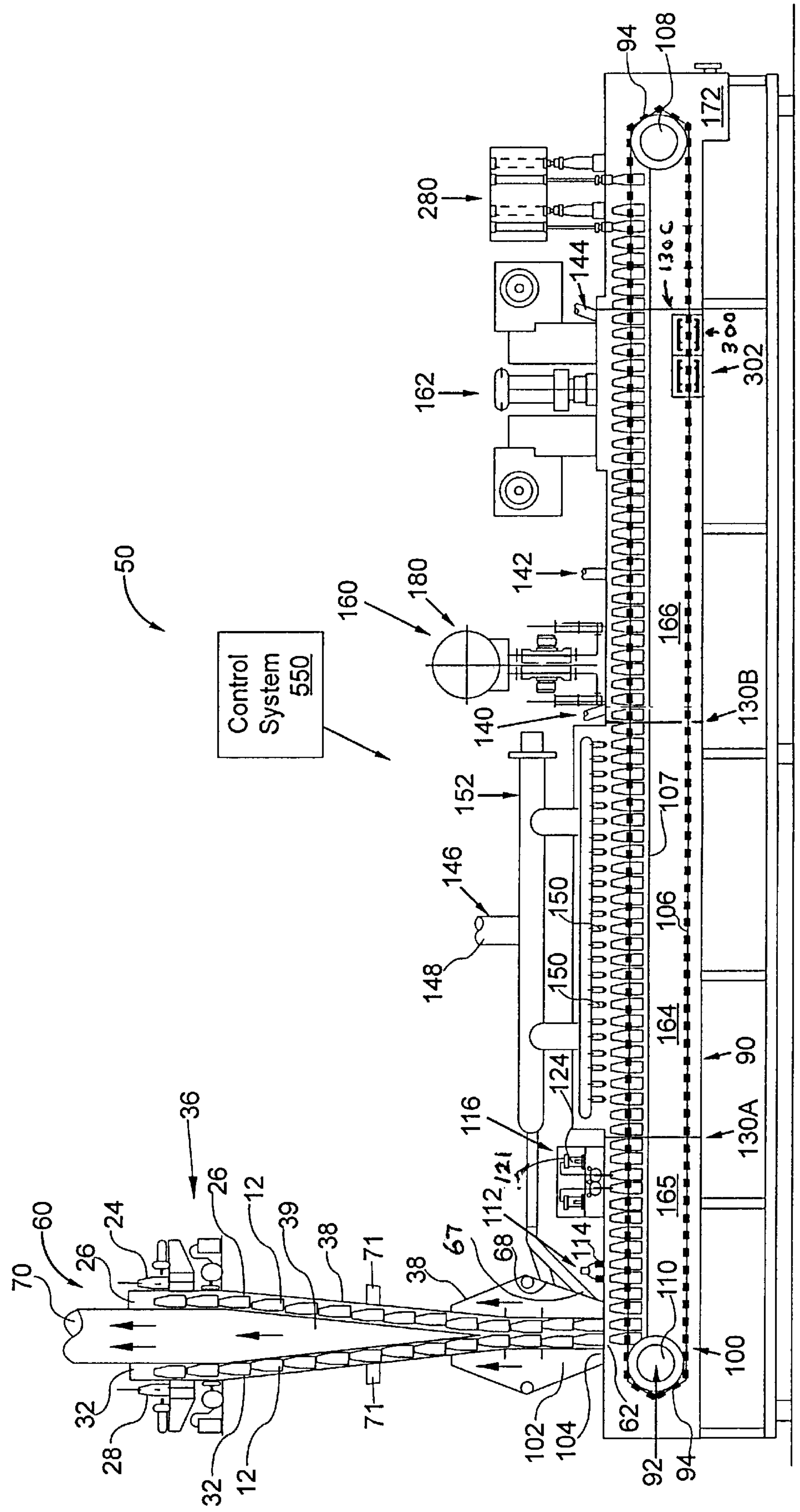
FIG. 3 is a partial cross-sectional side view of the aseptic processing apparatus of FIG. 1.

FIGS. 1—3 illustrate several views of an aseptic processing apparatus 10 in accordance with a preferred embodiment of the present invention. As shown, the aseptic processing apparatus 10 includes a first bottle unscrambler 20, a second bottle unscrambler 30, and a bottle lifter 40 for providing a supply of properly oriented empty bottles. The empty bottles are delivered to a filler apparatus 50 after passing through a bottle infeed and sterilization apparatus 60 for aseptic sterilization. The filled bottles are sealed at a first capping apparatus 400 or a second capping apparatus 410. A control system 550 monitors and controls the operation of the aseptic processing apparatus 10. The filled and sealed bottles are packed and palletized using a first case packing apparatus 480, a second case packing apparatus 490, a first palletizer 500, and a second palletizer 510.

The bottles 12 arrive at a first bottle unscrambler 20 with a random orientation, such that an opening 16 (see FIG. 8) of each bottle 12 can be oriented in any direction. The first bottle unscrambler 20 manipulates the bottles 12 until the opening 16 of each bottle 12 is in a top vertical position. The bottles 12 leave the first bottle unscrambler 20 in a series formation with the opening 16 of each bottle 12 oriented vertically. The bottles 12 travel in single file in a first lane 18 to a first bottle lifter 40. The first bottle lifter 40 lifts and transports the bottles 12 to a bottle infeed and sterilization apparatus 60. A second bottle unscrambler 30 may also used to provide a supply of vertically oriented bottles 12. The bottles 12 output from the second bottle unscrambler 30 travel in single file in a second lane 22 to a second bottle lifter 42, which lifts and transports the bottles 12 to the bottle infeed and sterilization apparatus 60.

Figure 4:
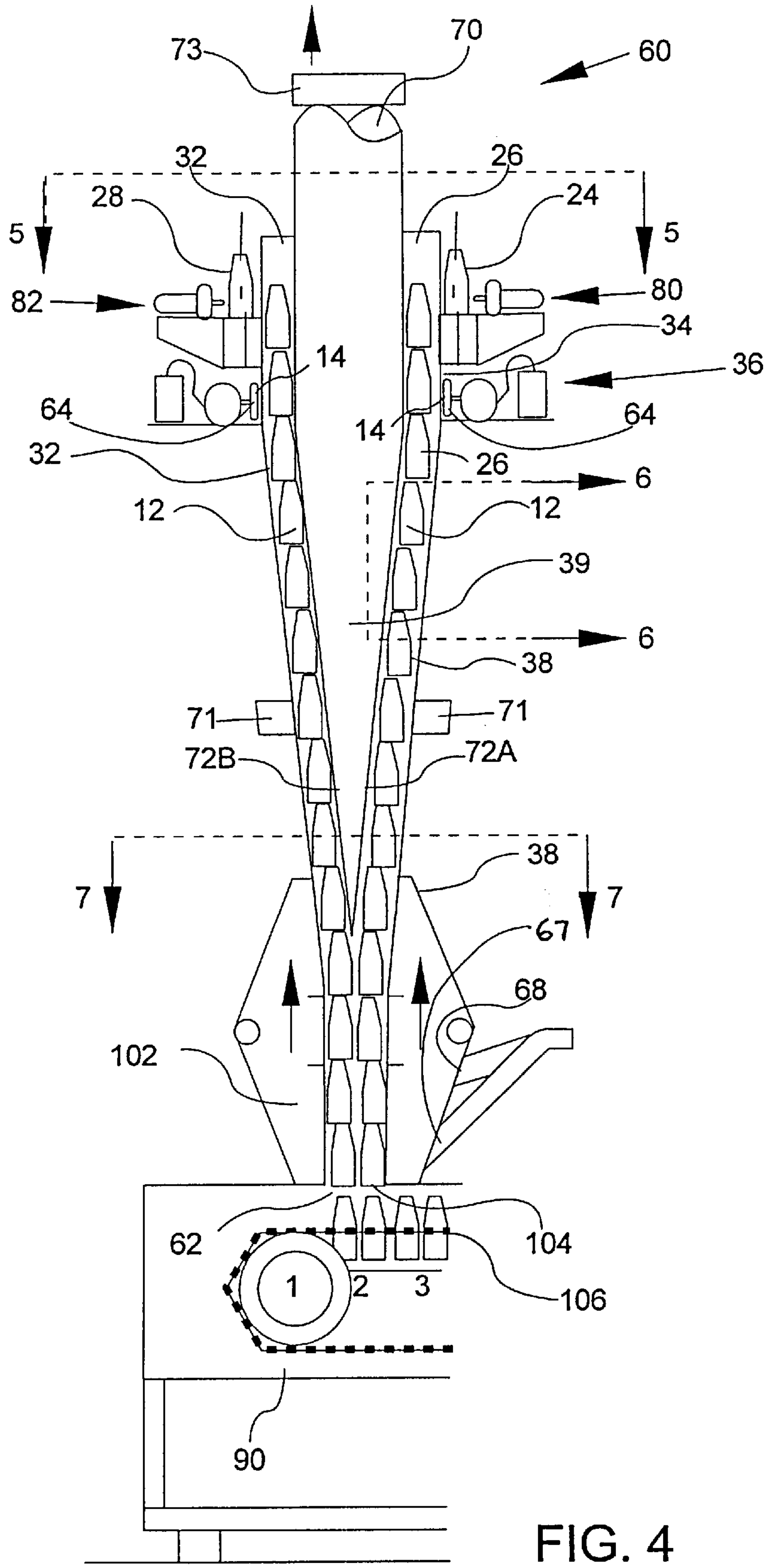
FIG. 4 is a cross-sectional side view of a bottle infeed and sterilization apparatus.
Figure 5:
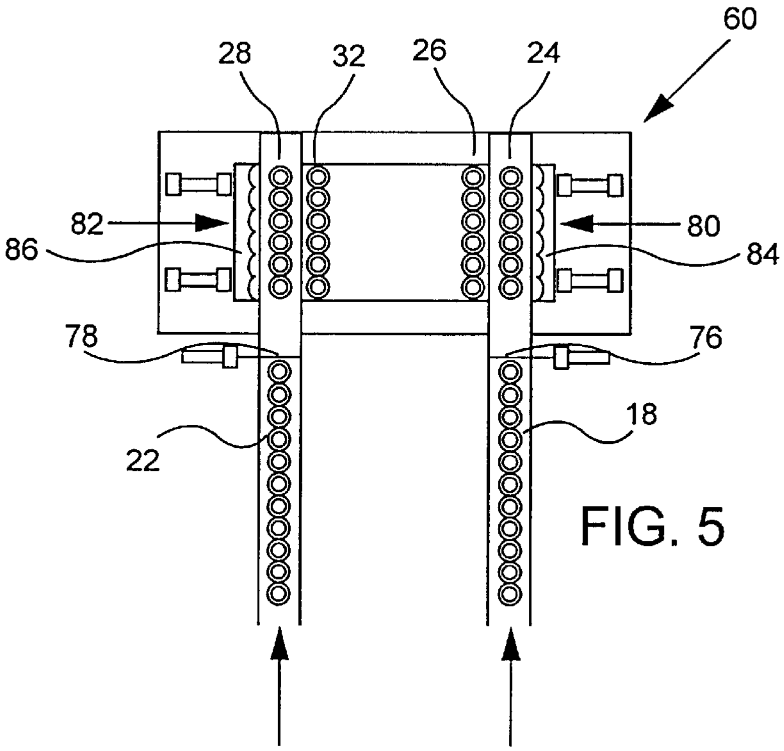
FIG. 5 illustrates a cross-sectional top view of the bottle infeed and sterilization apparatus taken along line 5—5 of FIG. 4.

FIG. 3 illustrates the bottle infeed, sterilization, and conveying apparatus 60 attached to the filler apparatus 50. FIG. 4 illustrates a cross-sectional side view of the bottle infeed, sterilization, and conveying apparatus 60. FIG. 5 illustrates a cross-sectional top view of the bottle infeed, sterilization, and conveying apparatus 60 taken along line 5—5 of FIG. 4. The bottle infeed and sterilization apparatus 60 preferably inputs six bottles 12 in a horizontal direction from the first lane 18 and six bottles in a horizontal direction from the second lane 22 (FIG. 5). A gate 76 in the first lane 18 selectively groups six bottles 12 at a time in first horizontal row 24. A gate 78 in the second lane 22 selectively groups six bottles 12 at a time in a second horizontal row 28. An infeed apparatus 80 includes a pushing element 84 for pushing the bottles 12 in the first horizontal row 24 into a first vertical lane 26. A corresponding infeed apparatus 80 includes a pushing element 86 for pushing the bottles 12 in the second horizontal row 28 into a second vertical lane 32. The six bottles 12 in the first vertical lane 26 and the six bottles 12 in the second vertical lane 32 are directed downward into the bottle infeed and sterilization apparatus 60.

Referring to FIG. 4, as the bottles 12 move downward in the first vertical lane 26 and the second vertical lane 32, a sterilant 14, such as heated hydrogen peroxide, oxonia, or other aseptic sterilant, is applied to an outside surface 34 of each bottle 12 by a sterilant application apparatus 36. The outside surface 34 of a bottle 12 is illustrated in greater detail in FIG. 8. The bottles 12 may move downward in the first vertical lane 26 and the second vertical lane 32 by the force of gravity. Alternatively, controlled downward movement of the bottles 12 can be created by the use of a conveying device such as a moving conveying chain. A plurality of pins are attached to the conveying chain. Each bottle 12 rests on one of the pins attached to the conveying chain. Therefore, the motion of each bottle is controlled by the speed of the moving conveying chain.

A sterilant such as hydrogen peroxide may be provided to the sterilant application apparatus 36 in many ways. For example, liquid hydrogen peroxide may be provided in a reservoir at a level maintained by a pump and overflow pipe. A plurality of measuring cups (e.g., approximately 0.5 ml each) connected by an air cylinder are submerged into the reservoir and are lifted above the liquid level. Thus, a measured volume of liquid hydrogen peroxide is contained in each measuring cup.

Each measuring cup may include a conductivity probe that is configured to send a signal to the control system 550 indicating that the measuring cup is full. A tube (e.g., having a diameter of about 1/16") is positioned in the center of the measuring cup. A first end of the tube is positioned near the bottom of the measuring cup. A second end of the tube is connected to the sterilant application apparatus 36. The sterilant application apparatus 36 includes a venturi and a heated double tube heat exchanger. When the measuring cup is full, and a signal is received from the control system 550, a valve is opened allowing pressurized sterile air to enter the venturi. The pressurized air flow causes a vacuum to be generated in second end of the tube causing liquid hydrogen peroxide to be pulled out of the measuring cup. The liquid hydrogen peroxide is sprayed into a sterile air stream which atomizes the hydrogen peroxide into a spray. The atomized hydrogen peroxide enters the double tube heat exchanger in order to heat the atomized hydrogen peroxide above its vaporization phase. The double tube heat exchanger is heated with steam and the temperature is monitored and controlled by the control system 550. In FIG. 4, the application of the sterilant 14 by the sterilant application apparatus 36 is accomplished through the use of spray nozzles 64 that produce a sterilant fog which is directed to the entire outside surface 34 of each bottle 12.

Alternatively, a direct spray of heated hydrogen peroxide may be continuously applied to the outside surface 34 of each bottle 12. For producing the direct spray, a metering pump regulates the amount of hydrogen peroxide, a flow meter continuously measures and records the quantity of hydrogen peroxide being dispensed, a spray nozzle produces a fine mist, and a heat exchanger heats the hydrogen peroxide above the vaporization point.

FIGS. 3 and 4 illustrate the sterilization chamber 38 for activation and drying of bottles 12 which is included in the bottle infeed, sterilization, and conveying apparatus 60. The sterilization chamber 38 sterilizes the outside surface 34 of each bottle 12. The sterilization chamber 38 encloses a conduit 39. Sterile heated air, which is generated by a sterile air supply system 146 (FIG. 3), enters the conduit 39 of the sterilization chamber 38 through ports 67 and 68 located at the bottom of the sterilization chamber 38. The sterile heated air also enters through a bottom opening 62 of the bottle infeed and sterilization apparatus 60. The sterile heated air travels up through the conduit 39 of the sterilization chamber 38, and exits the top of the sterilization chamber 38 through an exhaust conduit 70. The sterile heated air continuously flows in an upward direction through the sterilization chamber 38, thus preventing any contaminants from entering the bottle infeed and sterilization apparatus 60. To create the sterile heated air, the air is first passed through a filtering system (e.g., a group of double sterile air filters to sterilize the air. The air is then heated in a heating system (e.g., an electric heater) to about 230° F. The air temperature is regulated by the control system 550. Other techniques for providing the sterile heated air may also be used. The control system 550 monitors the air pressure and flow rate of the sterile heated air to ensure that an adequate flow of the hot sterile air is maintained in the bottle sterilization chamber 38 of the bottle infeed and sterilization apparatus 60.

Figure 6:
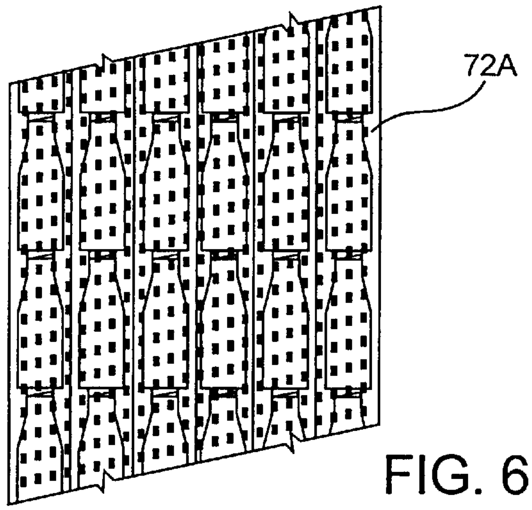
FIG. 6 is an interior sectional view of an interior wall taken along line 6—6 of FIG. 4.
Figure 7:
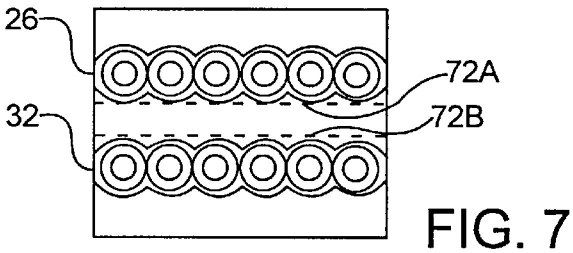
FIG. 7 is a cross-sectional view of the bottle infeed and sterilization apparatus taken along line 7—7 of FIG. 4.

As illustrated in FIGS. 4, 6, and 7, the sterilization chamber 38 includes two opposing, interior, perforated walls 72A, 72B. The perforated walls 72A and 72B guide the bottles 12 downward in the first vertical lane 26 and the second vertical lane 32, respectively. The perforated walls 72A, 72B also allow the complete circulation of hot sterile air around the outside surface 34 of each bottle 12 in the sterilization chamber 38. The sterilization chamber 38 supplies hot sterile air to the outside surface 34 of each bottle 12 between the sterilant application apparatus 36 and the bottom opening 62 of the bottle infeed and sterilization apparatus 60. This sterilant may be hydrogen peroxide or oxonia (hydrogen peroxide and peroxyacetic acid).

In accordance with the preferred embodiment of the present invention, twelve drying positions are provided in the sterilization chamber 38. Each bottle 12 is exposed to the hot sterile air in the sterilization chamber 38 for about at least 24 seconds. This provides time sufficient time for the hydrogen peroxide sterilant to break down into water and oxygen, to kill any bacteria on the bottles 12, and to evaporate from the outside surface 34 of the bottles 12.

An exhaust fan 73 is located at a top of the exhaust conduit 70 to provide an outlet from the sterilization tunnel 90, and to control the sterile air flow rate through the sterilization chamber 38. The exhaust fan 73 is controlled by the control system-550. The control system 550 controls the sterile air temperature preferably to about 230° F., and controls the sterile air flow rate through the sterilization chamber 38. The flow rate is preferably about 1800 scfm through the sterilization chamber 38. The bottles 12 leave the sterilization chamber 38 with a hydrogen peroxide concentration of less than 0.5 PPM.

As shown in FIGS. 3 and 4, a plurality of proximity sensors 71 located along the sides of the vertical lanes 26, 32 detect any bottle 12 jams that occur within the sterilization chamber 38. The proximity sensors 71 transmit an alarm signal to the control system 550. The bottles 12 leave the bottle infeed and sterilization apparatus 60 through the bottom opening 62, and enter a sterilization tunnel 90 of the filler apparatus 50.

Figure 8:
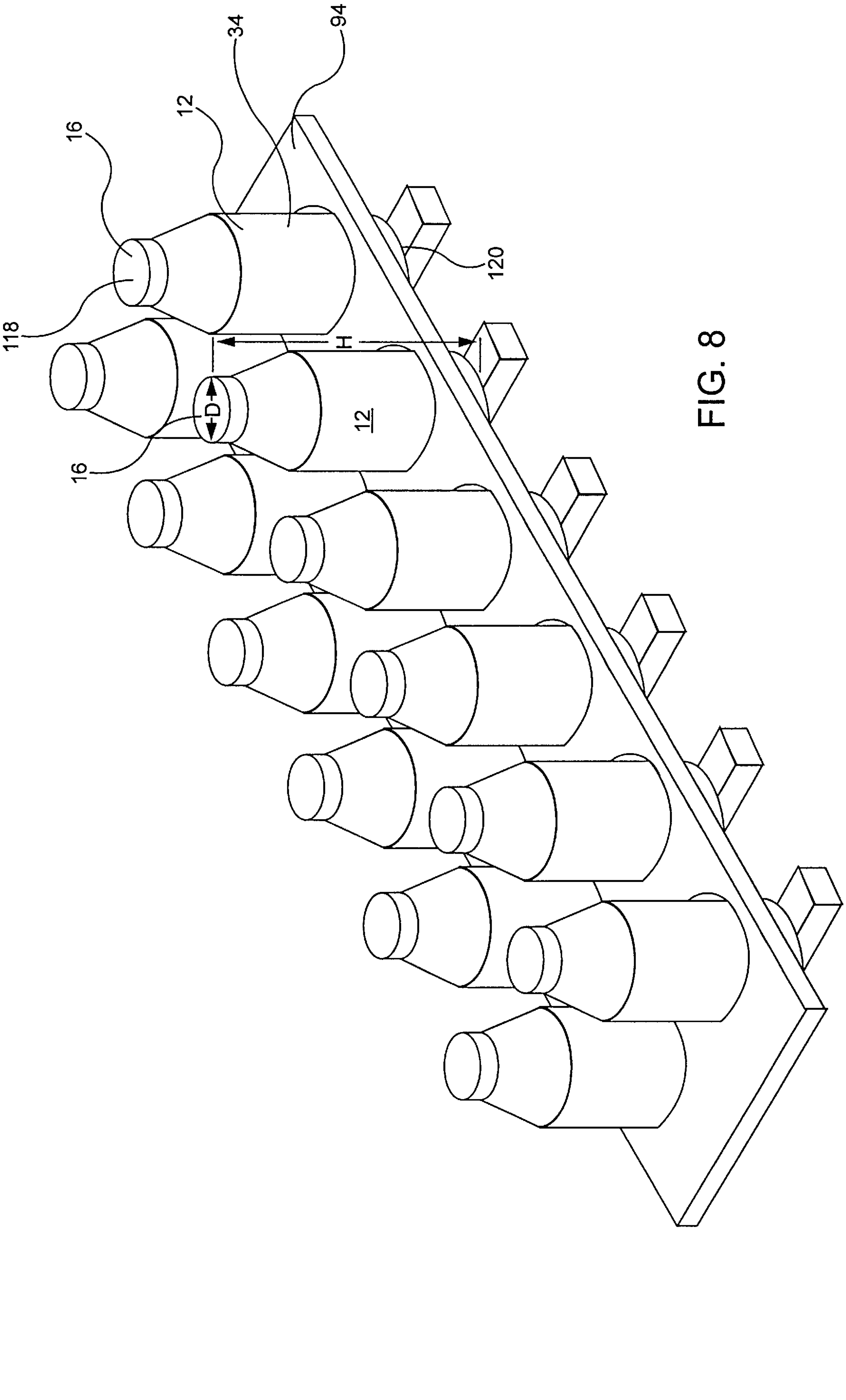
FIG. 8 is a perspective view of a conveying plate for use in the aseptic processing apparatus of the present invention.

In the preferred embodiment of the present invention, the filler apparatus 50 includes forty-one (41) index stations 92, hereafter referred to as "stations." Various index stations 92 are illustrated in FIGS. 3, 4, and 11–15. The conveying motion of the bottles 12 to the various stations 92 through the filler apparatus 50 is based on an indexing motion. The filler apparatus 50 is designed to convey the bottles 12 through the various operations of the filler 50 in a two by six matrix. The twelve bottles 12 in the two by six matrix are positioned in, and displaced by, a conveying plate 94 as illustrated in FIG. 8. Therefore, twelve bottles 12 are exposed to a particular station 92 at the same time. A conveying apparatus 100 moves the set of twelve bottles 12 in each conveying plate 94 sequentially through each station 92.

Referring to FIGS. 3 and 4, the bottles 12 are supplied from an infeed chamber 102 to station 2 of the filler apparatus 50 through the bottom opening 62 of the bottle infeed and sterilization apparatus 60. The infeed chamber 102 is enclosed to direct heated hydrogen peroxide laden air completely around the outer surface 34 of the bottles 12. A mechanical scissors mechanism and a vacuum "pick and place" apparatus 104 position twelve bottles 12 at a time (in a two by six matrix, FIG. 8) into one of the conveying plates 94.

A plurality of conveying plates 94 are attached to a main conveyor 106. The main conveyor 106 forms a continuous element around conveyor pulleys 108 and 110 as illustrated in FIG. 3. A bottle support plate 107 supports a bottom 120 of each bottle 12 as the bottles 12 are conveyed from station to station through the filler apparatus 50. Each conveying plate 94 passes through stations 1 through 41, around pulley 108, and returns around pulley 110 to repeat the process. The main conveyor 106, conveying plates 94, and pulleys 108 and 110 are enclosed in the sterilization tunnel 90.

At station 4, the bottles 12 in the conveying plate 94 enter a bottle detection apparatus 112. The bottle detection apparatus 112 determines whether all twelve bottles 12 are actually present and correctly positioned in the conveying plate 94. Proximity sensors 114 detect the presence and the alignment of each bottle 12. In the present invention, a bottle 12 with correct alignment is in an upright position with the opening 16 of the bottle 12 located in an upward position. Information regarding the location of any misaligned or missing bottles 12 is relayed to the control system 550. The control system 550 uses this location information to ensure that, at future stations 92, bottle filling or sealing will not occur at the locations corresponding to the misaligned or missing bottles 12.

Figure 10:
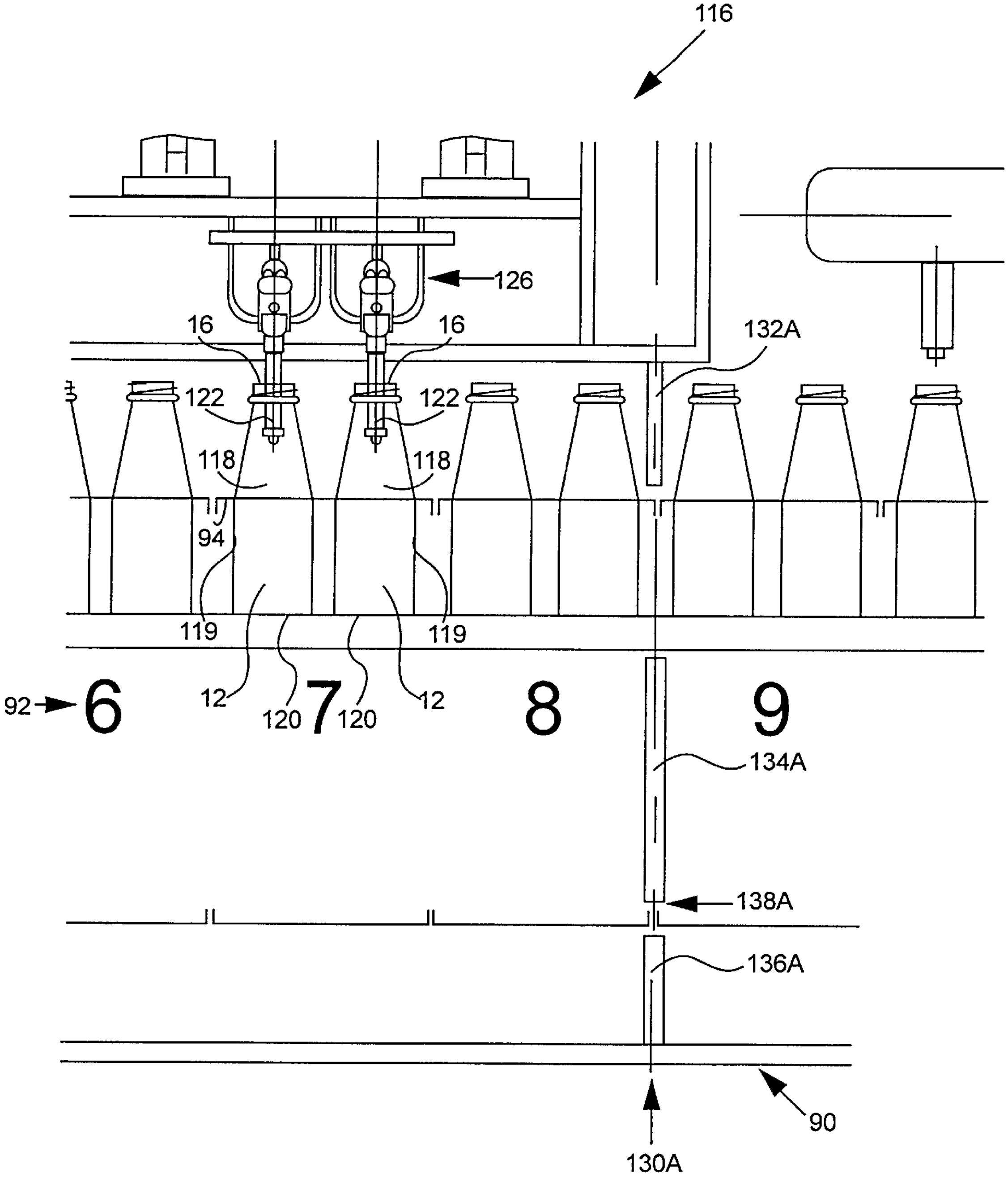
FIG. 10 is a cross-sectional side view of an interior bottle sterilization apparatus and the partition located between stations 8 and 9.

At station 7, as illustrated in FIGS. 3 and 10, the bottles 12 in the conveying plate 94 enter an interior bottle sterilization apparatus 116. A sterilant, such as hydrogen peroxide, oxonia, or any other suitable aseptic sterilant is applied as a heated vapor fog into the interior 118 of each bottle 12. Preferably, hydrogen peroxide is used as the sterilant in the present invention. The application of sterilant is accomplished with the use of a plurality of sterilant measuring devices 121 and applicator spray nozzles 122. A separate measuring device 121 and applicator spray nozzle 122 are used for each of the twelve bottle 12 locations in the conveying plate 94. Each bottle 12 is supplied with the same measured quantity of sterilant, preferably in the form of a hot vapor fog. The measured quantity of sterilant may be drawn from a reservoir 124 of sterilant, heated, vaporized, etc., in a manner similar to that described above with regard to the sterilant application apparatus 36.

The control system 550 monitors and controls a spray apparatus 126 that includes the applicator spray nozzles 122. Each applicator spray nozzle 122 sprays the sterilant into the interior 118 of a corresponding bottle 12 as a hot vapor fog. The applicator spray nozzles 122 are designed to extend through the bottle openings 16. The applicator spray nozzles 122 descends into the interior 118 and toward the bottom of the bottles 12. This ensures the complete application of sterilant to the entire interior 118 and interior surface 119 of each bottle 12. Alternately, the applicator spray nozzles 122 may be positioned immediately above the bottle openings 16 prior to the application of sterilant.

Figure 9:
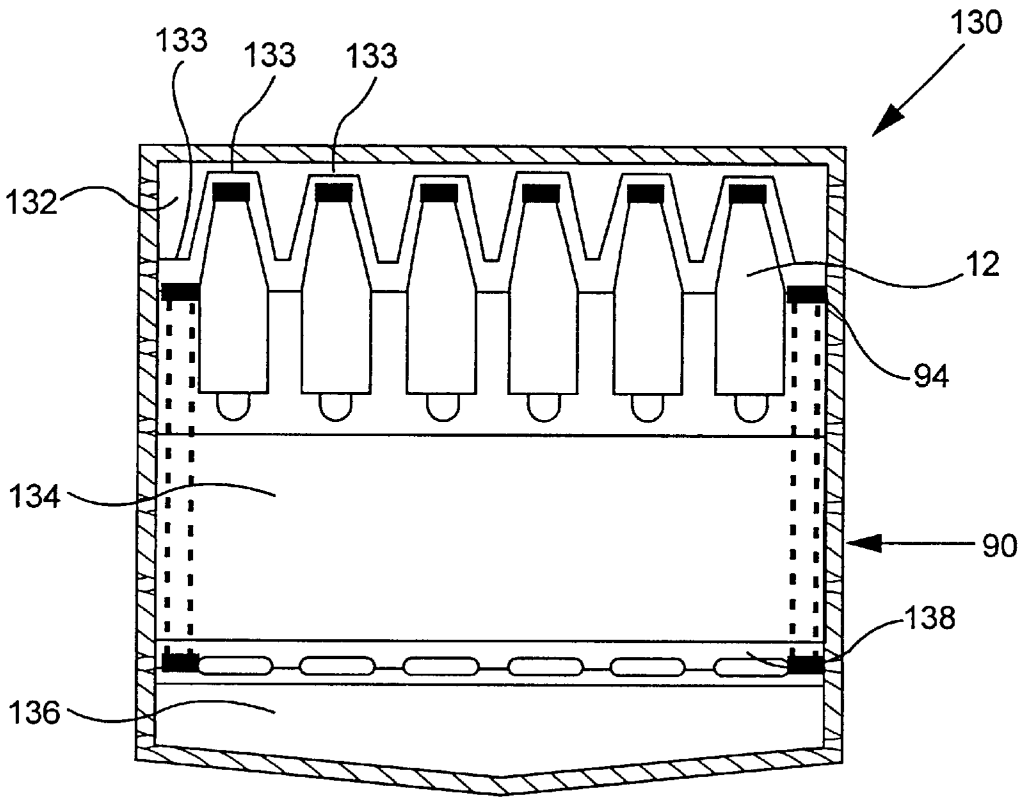
FIG. 9 is a perspective view of a partition in a sterilization tunnel.

FIG. 9 illustrates a perspective view of a partition 130 that provides control of sterile air flow within the sterilization tunnel 90 of the filler apparatus 50. The partition 130 includes a top baffle plate 132, a middle baffle plate 134, and a bottom baffle plate 136. The top baffle plate 132 and the middle baffle plate 134 are provided with cut-outs 133 which correspond to the outer shape of each bottle 12 and to the outer shape of the conveyor plate 94. The cut-outs 133 allow each bottle 12 and each conveyor plate 94 to pass through the partition 130. A space 138 between the middle baffle plate 134 and the bottom baffle plate 136 allows each empty conveyor plate 94 to pass through the partition 130 as it travels on its return trip from the pulley 108 toward the pulley 110.

Figure 11:
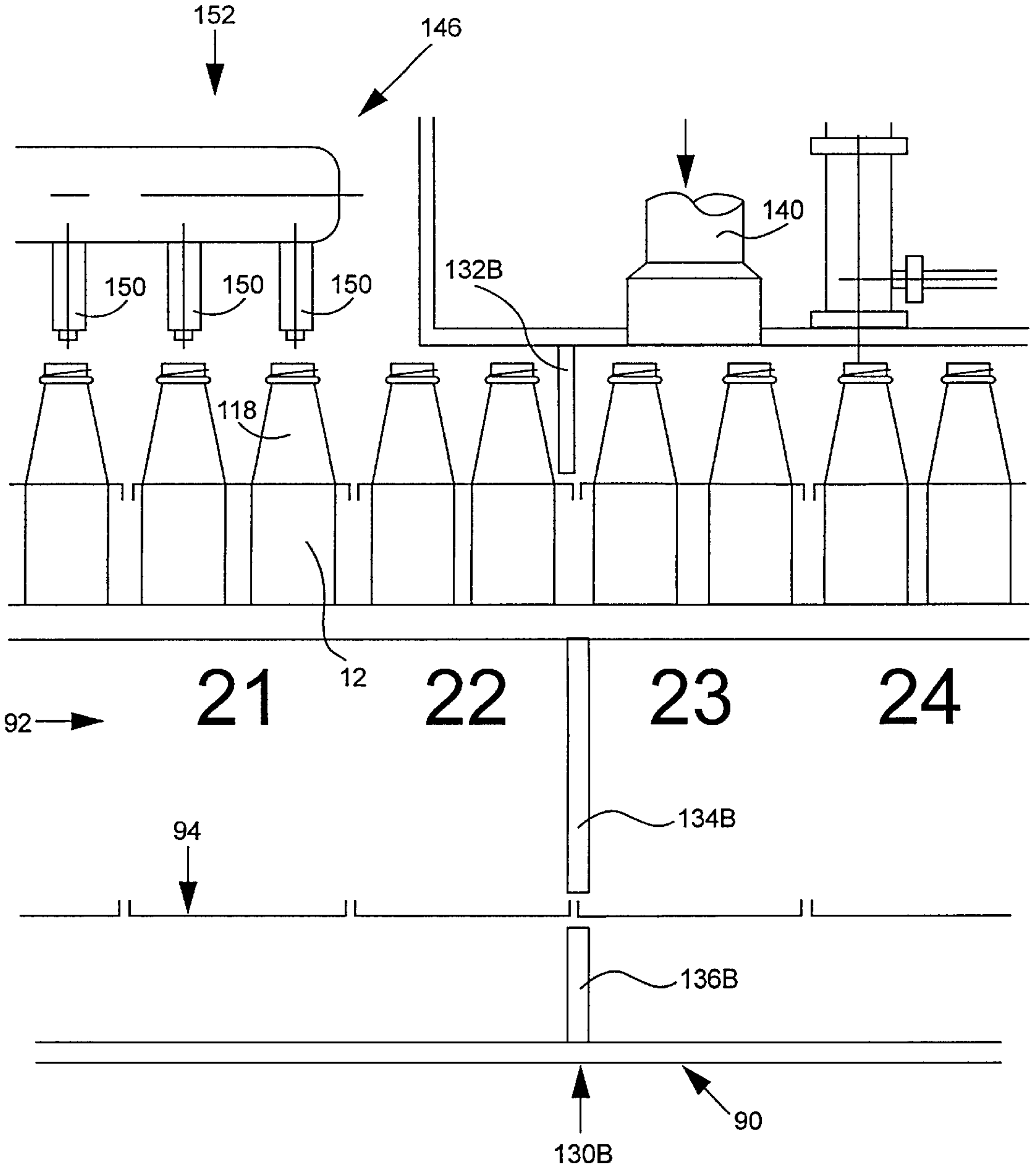
FIG. 11 is a cross-sectional side view of the partition located between stations 22 and 23.
Figure 12:
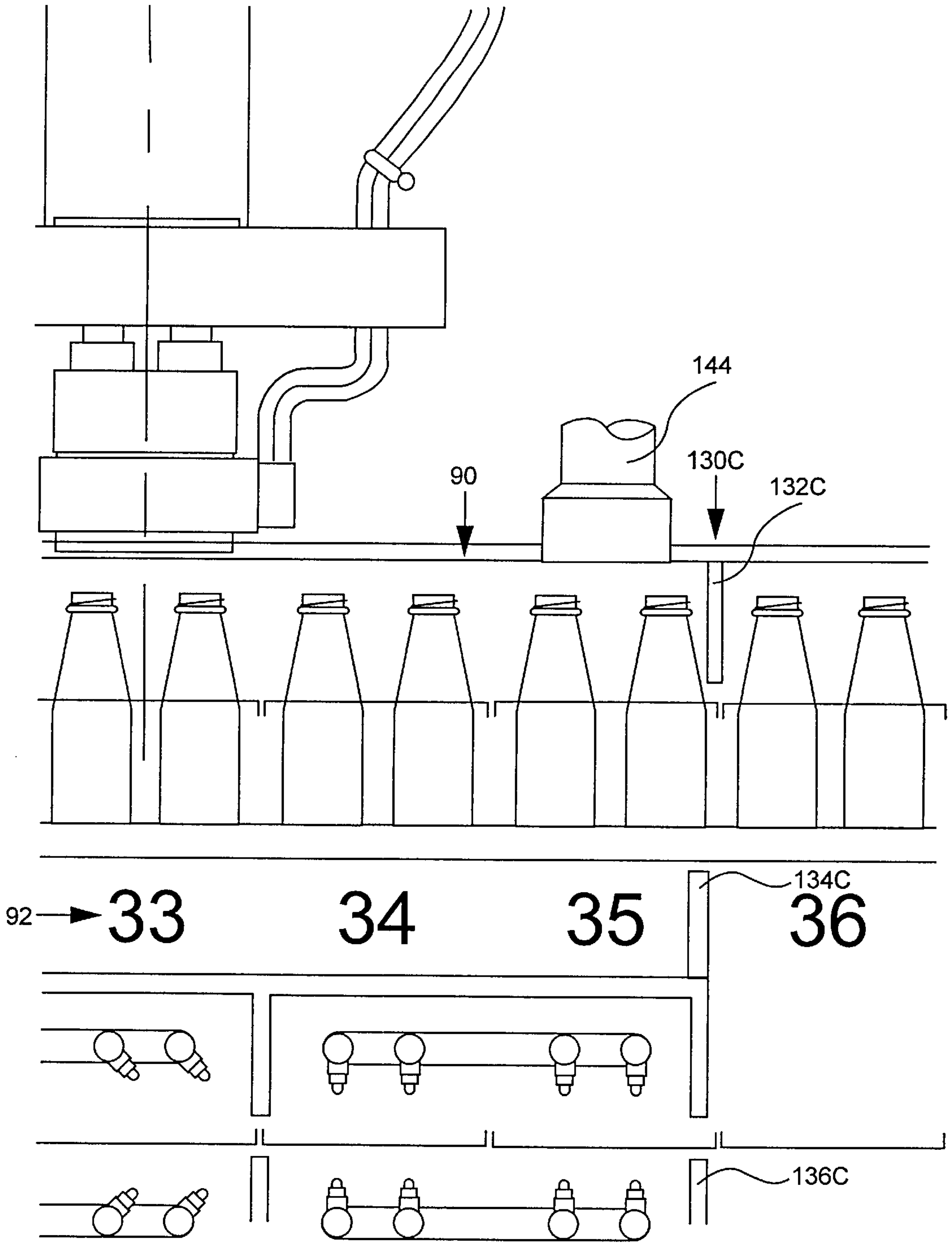
FIG. 12 is a cross-sectional side view of the partition located between stations 35 and 36.

As illustrated in FIG. 3, partitions 130A, 130B, and 130C, are located within the sterilization tunnel 90. FIG. 10 illustrates a cross-sectional view of partition 130A including baffle plates 132A, 134A, and 136A. The partition 130A is located between stations 8 and 9. FIG. 11 illustrates a cross-sectional view of partition 130B including baffle plates 132B, 134B, and 136B. The partition 130B is located between stations 22 and 23. FIG. 12 illustrates a cross-sectional view of partition 130C including baffles 132C, 134C, and 136C. The partition 130C is located between stations 35 and 36. As illustrated in FIG. 3, sterile air is introduced through sterile air supply sources (e.g., conduits 140, 142, and 144) into the sterilization tunnel 90. The sterile air conduit 140 is located at station 23 (FIG. 11), the sterile air conduit 142 is located at station 27 (FIG. 3), and the sterile air conduit 144 is located at station 35 (FIG. 12).

The partition 130A separates an activation and drying apparatus 152 from the interior bottle sterilization apparatus 116. The partition 130B separates the activation and drying apparatus 152 from a main product filler apparatus 160 and a lid sterilization and heat sealing apparatus 162. Thus, a first sterilization zone 164 is created that includes the activation and drying apparatus 152. Partition 130C separates the main product filler apparatus 160 and the lid sterilization and heat sealing apparatus 162 from a bottle discharge apparatus 280. Thus, partitions 130B and 130C create a second sterilization zone 166 that includes the main product filler apparatus 160 and the lid sterilization and heat sealing apparatus 162. A third sterilization zone 172 includes the bottle discharge apparatus 280. A fourth sterilization zone 165 includes the interior bottle sterilization apparatus 116. The second sterilization zone 166 provides a highly sterile area where the bottles 12 are filled with a product and sealed. The second sterilization zone 166 is at a higher pressure than the first sterilization zone 164 and the third sterilization zone 172. Therefore, any gas flow leakage is in the direction from the second sterilization zone 166 out to the first sterilization zone 164 and the third sterilization zone 172. The first sterilization zone 164 is at a higher pressure than the fourth sterilization zone 165. Therefore, gas flow is in the direction from the first sterilization zone 164 to the fourth sterilization zone 165.

The partitions 130A, 130B, and 130C create sterilization zones 164, 165, 166, and 172 with different concentration levels of gas laden sterilant (e.g., hydrogen peroxide in air). The highest concentration level of sterilant is in the fourth sterilization zone 165. For example, with the sterilant hydrogen peroxide, the concentration level of hydrogen peroxide is about 1000 ppm (parts per million) in the fourth sterilization zone 165. The hydrogen peroxide sterilant level is about 3 ppm in the first sterilization zone 164. The lowest concentration level of sterilant is in the second sterilization zone 166. In the second sterilization zone 166, the hydrogen peroxide sterilant concentration level is less than 0.5 ppm and typically about 0.1 ppm. Advantageously, this helps to maintain the main product filler apparatus 160 and the lid sterilization and heat sealing apparatus 162 at a low sterilant concentration level. This prevents unwanted high levels of sterilant to enter the food product during the filling and lidding process. The hydrogen peroxide sterilant concentration level is about 0.1 ppm in the third sterilization zone 172.

Figure 14:
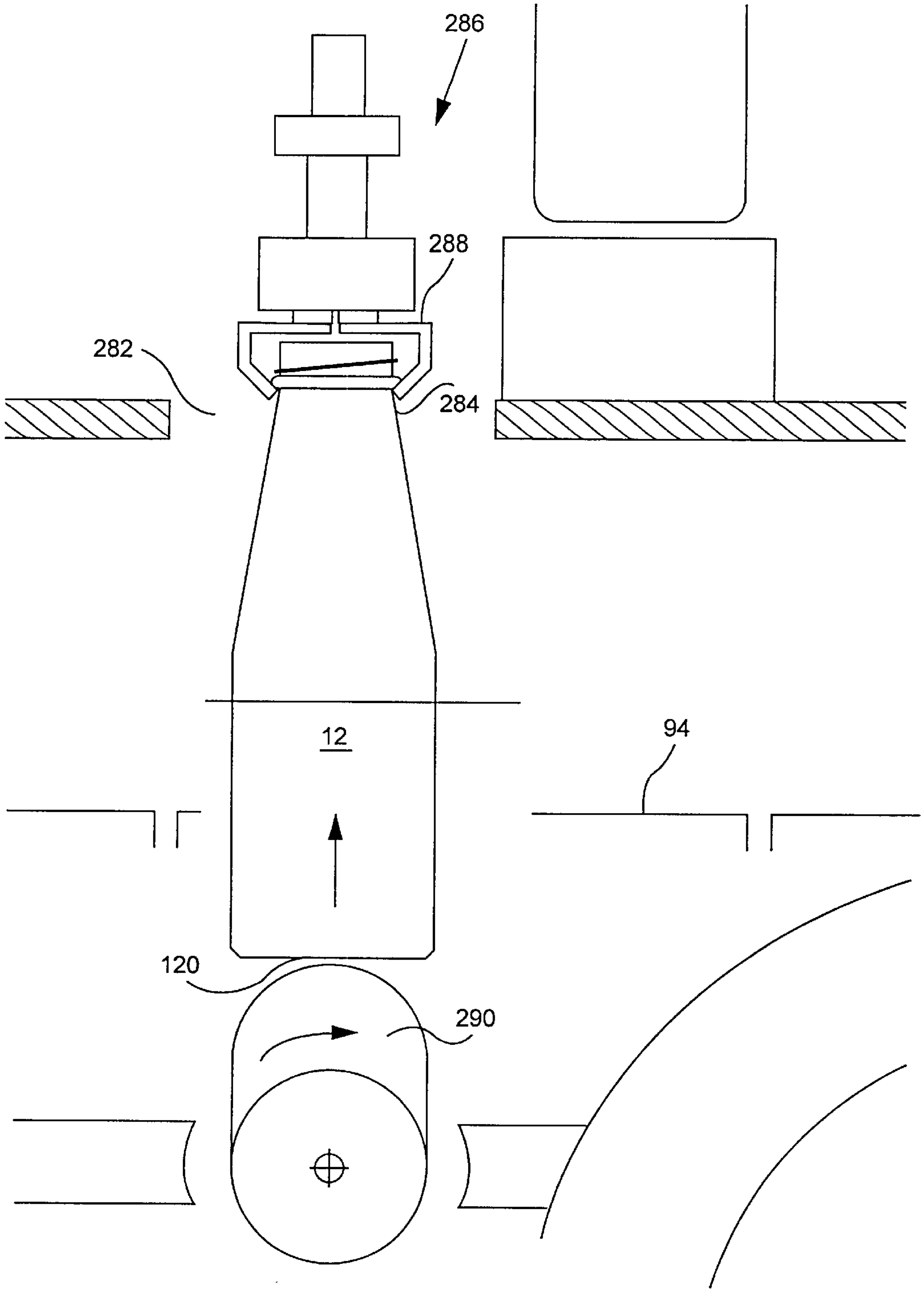
FIG. 14 is a side view of a lifting apparatus with a gripper mechanism for lifting the bottles from the sterilization tunnel.
Figure 15:
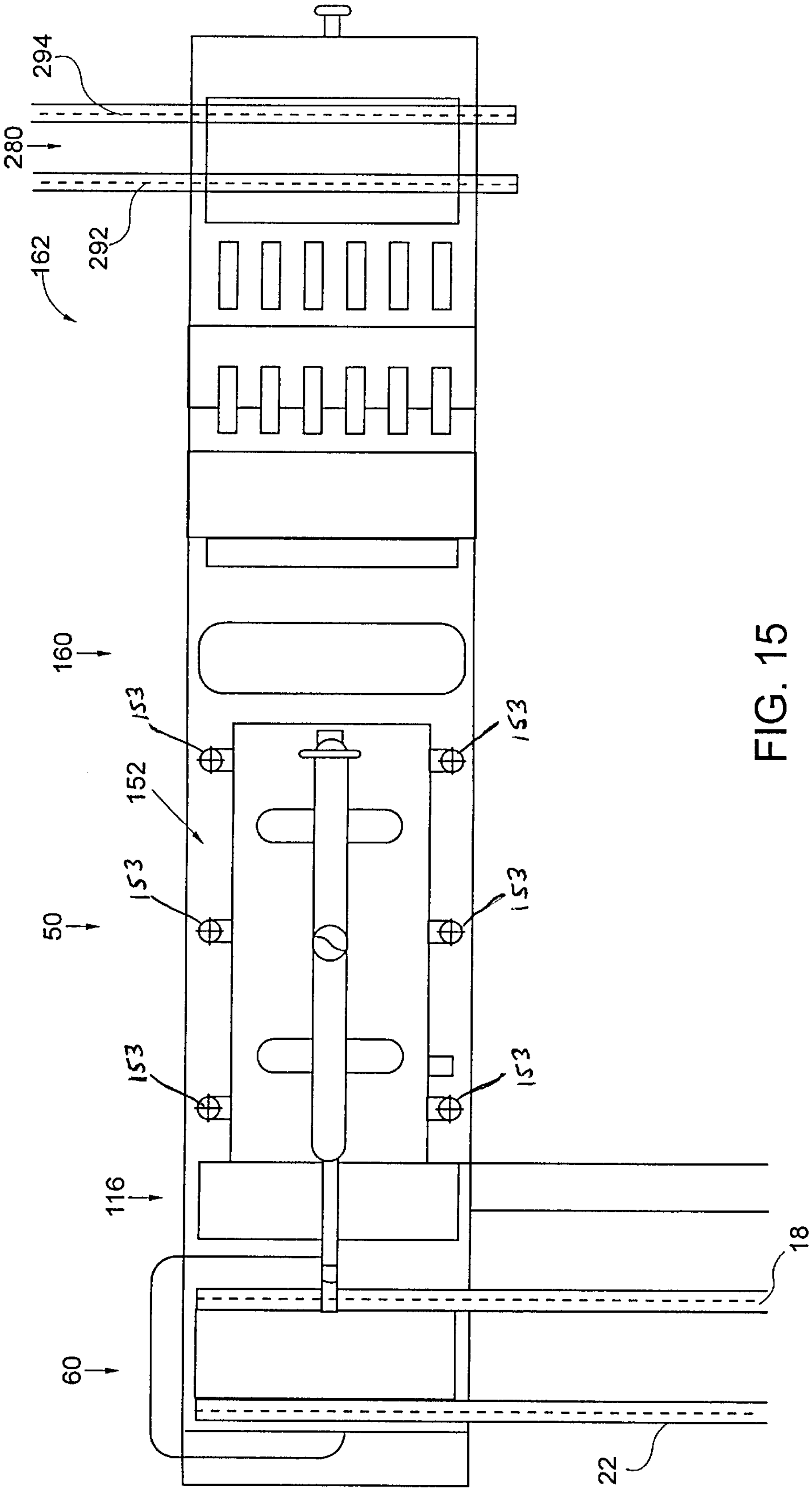
FIG. 15 is a top view of the aseptic processing apparatus.

As illustrated in FIG. 3, a gas such as hot sterile air enters the first sterilization zone 164 at a rate of about 2400 cfm (cubic feet per minute). The temperature of the hot sterile air is about 230° F. The hot sterile air enters the first sterilization zone 164 through conduit 148. Additional hot sterile air enters the second sterile zone through sterile air conduits 140, 142, and 144 at a total rate of about 1000 cfm (FIG. 3). Also, hot sterile air enters at a rate of about 1800 cfm through ports 67 and 68 leading into the infeed and sterilization apparatus 60. A portion of the hot sterile air exits the sterilization tunnel 90 at a rate of about 1500 cfm through a plurality of exhaust ports 153 located in the first sterilization zone 164 (FIG. 15). A portion of the hot sterile air exits the sterilization tunnel 90 at a rate about 100 cfm through an opening 282 (FIG. 14). The bottles 12 exit the sterilization tunnel 90 through the opening 282. The continuous flow of sterile air flow out through the opening 282 prevents contaminants from entering the sterilization tunnel 90.

As illustrated in FIG. 3, the hot sterile air is drawn out of the fourth sterilization zone 165 of the sterilization tunnel 90 through the bottom opening 62 in the bottle infeed and sterilization apparatus 60. Next, the hot sterile air from the infeed and sterilization apparatus together with the fourth sterilization zone 165 exits out of the exhaust conduit 70 of the infeed and sterilization apparatus at a rate of about 3600 cfm. This outflow of hot sterile air from the bottle infeed and sterilization apparatus 60 prevents contaminants from entering the bottle infeed sterilization apparatus 60 and the sterilization tunnel 90.

Stations 10 through 21 include twelve stations for directing hot sterile air into each bottle 12 for the activation and removal of the sterilant from the interior of the bottle 12. The sterile air supply system 146 supplies hot sterile air to a plurality of nozzles 150 in the activation and drying apparatus 152. Hot sterile air is supplied to the sterile air supply system 146 through conduit 148. The air is first passed through a filtration system to sterilize the air. The air is then heated in a heating system to about 230° F. The air temperature is regulated by the control system 550. Also, the control system 550 monitors the air pressure and flow rate to ensure that an adequate flow of hot sterile air is maintained in the sterilization tunnel 90 of the application and drying apparatus 152.

As shown in FIG. 8, each bottle 12 generally has a small opening 16 compared to its height "H." A ratio of a diameter "D" of the bottle 12 to the height "H" of the bottle 12 is generally less than 1.0. The small bottle opening 16 combined with a larger height "H" restricts the flow of hot gas into the interior 118 of the bottle 12. Also, PET and HDPE bottle materials have low heat resistance temperatures. These temperatures commonly are about 55° C. for PET and about 121° C. for HDPE. Typically, in the aseptic packaging industry, a low volume of air at a high temperature is applied to the packaging materials. This often results in deformation and softening of packaging materials formed of PET and HDPE. In order to prevent softening and deformation of the bottles 12, when formed from these types of materials, the present invention applies high volumes of air at relatively low temperatures over an extended period of time in the activation and drying apparatus 152. The plurality of nozzles 150 of the activation and drying apparatus 152 direct hot sterile air into the interior 118 of each bottle 12 (FIG. 11). A long exposure time is predicated by the geometry of the bottle 12 and the softening temperature of the material used to form the bottle 12. In the present invention, about 24 seconds are allowed for directing hot sterile air from the plurality of nozzles 150 into each bottle for the activation and removal of sterilant from the interior surface 119 of the bottle 12. To achieve aseptic sterilization, a minimum bottle temperature of about 131° F. should be held for at least 5 seconds. To achieve this bottle temperature and time requirements, including the time required to heat the bottle, the sterilant is applied for about 1 second and the hot sterile air is introduced for about 24 seconds. The hot sterile air leaves the nozzles 150 at about 230° F. and cools to about 131° F. when it enters the bottle 12. The hot sterile air is delivered at a high volume so that the bottle 12 is maintained at about 131° F. for at least 5 seconds. The about 24 seconds provides adequate time for the bottle 12 to heat up to about 131° F. and to maintain this temperature for at least 5 seconds. After bottle 12 has dried, the residual hydrogen peroxide remaining on the bottle 12 surface is less than 0.5 PPM.

A foodstuff product is first sterilized to eliminate bacteria in the product. An "Ultra High Temperature" (UHT) pasteurization process is required to meet the aseptic FDA standard. The time and temperature required to meet the aseptic FDA standard depends on the type of foodstuff. For example, milk must be heated to 282° F. for not less than 2 seconds in order to meet the aseptic standards.

Figure 13:
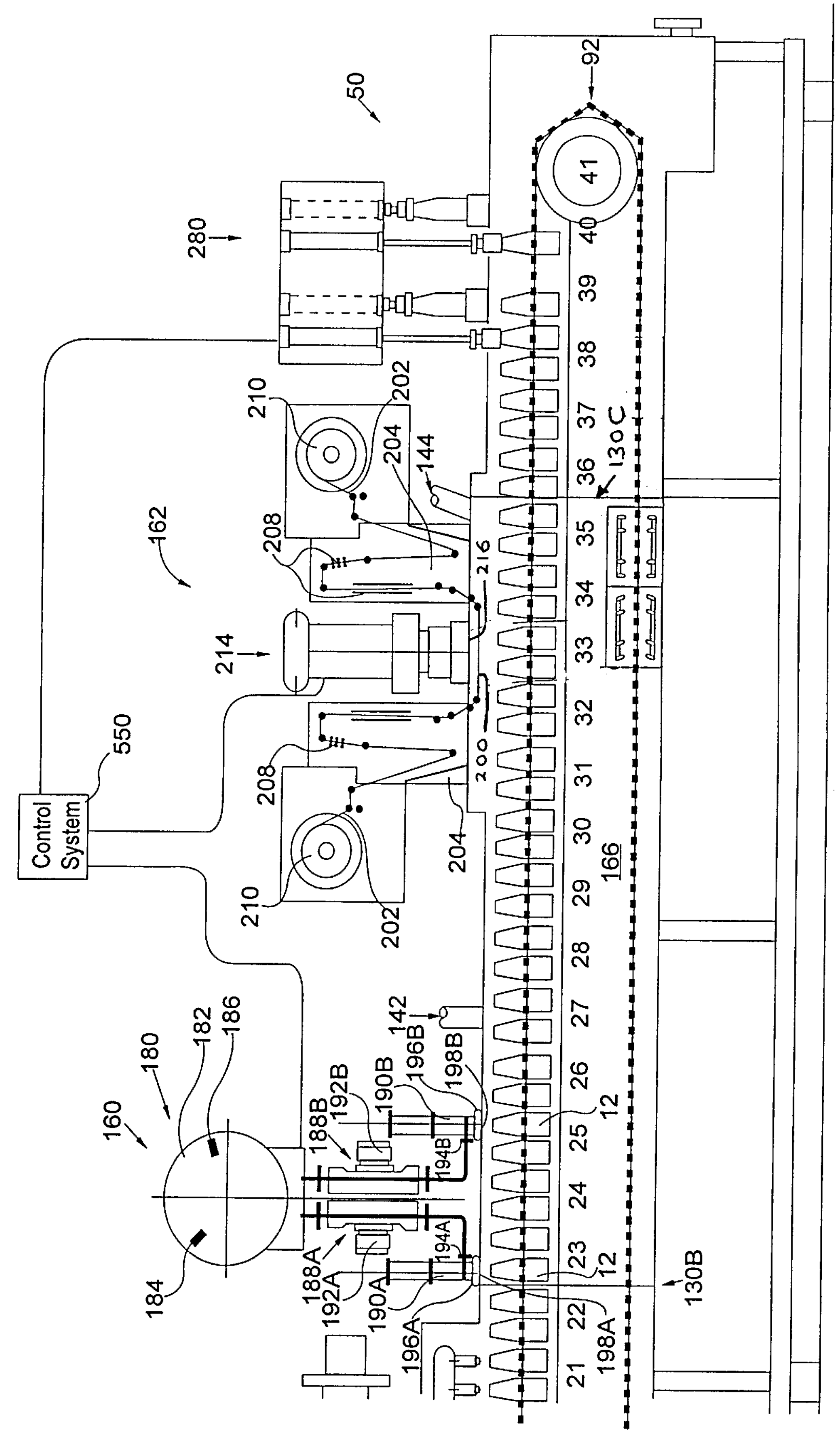
FIG. 13 is a cross-sectional side view of a lid sterilization and heat sealing apparatus.

After UHT pasteurization, the product is delivered to a main product filler apparatus 160. The main product filler apparatus is illustrated in FIGS. 3 and 13. The main product filler 160 can be sterilized and cleaned in place to maintain aseptic FDA and 3A standards. A pressurized reservoir apparatus 180 that can be steam sterilized is included in the main product filler apparatus 160. As illustrated in FIG. 13, the pressurized reservoir apparatus 180 includes an enclosed product tank 182 with a large capacity (e.g., 15 gallons). The product tank 182 is able to withstand elevated pressures of about 60 psig or more. The pressurized reservoir apparatus 180 also includes a level sensor 184, a pressure sensor 186, a volumetric measuring device 188, and a filling nozzle 190. The product tank 182 includes a single inlet with a valve cluster including a sterile barrier to separate the product process system from aseptic surge tanks and the main product filler apparatus 160. The product tank 182 has an outlet with twelve connections. At each connections is a volumetric measuring device 188 such as a mass or volumetric flow meter. A plurality of filling nozzles 190A, 190B are provided at stations 23, 25, respectively. In addition, there are a plurality of volumetric measuring devices 188A and 188B to measure the volume of product entering each bottle 12 at stations 23 and 25, respectively. The control system 550 calculates the desired volume of product to be inserted into each bottle 12, and controls the product volume by opening or closing a plurality of valves 194A and 194B. The activation mechanisms for valves 194A and 194B have a sterile barrier to prevent contamination of the product. The plurality of valves 194A control the volume of product flowing through a corresponding plurality of nozzles 196A into the bottles 12 at station 23. The plurality of valves 194B control the volume of product flowing through a corresponding plurality of nozzles 196B into the bottles 12 at station 25. The control system 550 uses the previously stored information provided by the bottle detection apparatus 112 to only allow filling to occur at the locations where bottles 12 are actually present and correctly aligned.

The initial sterilization process for the pressurized reservoir apparatus 180 includes the step of exposing all of the surfaces of the pressurized reservoir apparatus 180 that come in contact with the product to steam at temperatures above about 250° F. for a minimum of about 30 minutes. Elements such as cups 198A and 198B are used to block off nozzle outlets 196A and 196B respectively, to allow a build-up of steam pressure to about 50 psig inside the pressurized reservoir apparatus 180. Condensate generated as the steam heats the interior surfaces of the pressurized reservoir apparatus 180 is collected in the cups 198A and 198B. This condensate is released when the cups 198A and 198B are removed from the nozzle outlets 196A and 196B. Once the interior surfaces of the pressurized reservoir apparatus 180 are sterilized, the steam is shut off, and sterile air is used to replace the steam. The sterile air reduces the interior temperature of the pressurized reservoir apparatus 180 to the temperature of the product before the product is allowed to enter the enclosed product tank 182. Sterile air is directed through sterile air conduits 142 and 144 into the second sterilization zone 166 at a volume rate of about 800 scfm (FIG. 13). The sterile air flow entering the second sterilization zone 166 provides sterile air to the main product filler apparatus 160 and to the lid sterilization and heat sealing apparatus 162.

The main product filler apparatus 160 includes a separate filling position for each bottle. The bottle 12 filling operation is completed for six bottles at station 23 and for six bottles at station 25.

FIGS. 3 and 13 illustrate the lid sterilization and heat sealing apparatus 162. A lid 200 is applied to each of the twelve bottles 12 at station 31. For a fully aseptic bottle filler, complete lid 200 sterilization is necessary, and therefore a sterilant such as hydrogen peroxide is typically used. In the present invention, the lids are formed of a material such as foil or plastic. The lids 200 are joined together by a small interconnecting band that holds them together to form a long connected chain of lids 200, hereinafter referred to as a "daisy chain" 202. A daisy chain 202 of lids 200 is placed on each of a plurality of reels 210. For the twelve bottle configuration of the present invention, six of the reels 210, each holding a daisy chain 202 of lids 200, are located on each side of a heat sealing apparatus 214. Each daisy chain 202 of lids 200 winds off of a corresponding reel 210 and is sterilized, preferably using a hydrogen peroxide bath 204. A plurality of hot sterile air knives 208, which are formed by jets of hot sterile air, activate the hydrogen peroxide to sterilize the lids 200 on the daisy chain 202. The hot sterile air knives 208 also remove the hydrogen peroxide from the lids 200 so that the residual concentration of hydrogen peroxide is less than 0.5 PPM. The hydrogen peroxide bath 204 prevents any contaminants from entering the sterilization tunnel 90 via the lidding operation. Once sterilized, the lids 200 enter the sterilization tunnel 90 where they are separated from the daisy chain 202 and placed on a bottle 12. Each lid is slightly larger in diameter then that of the opening 16 of a bottle 12. During the placement of the lid 200 on the bottle 12, a slight mechanical crimp of the lid 200 is formed to locate and hold the lid 200 on the bottle 12. The crimp holds the lid 200 in place on the bottle 12 until the bottle 12 reaches a station 33 for sealing.

At station 33, the lids 200 are applied to the bottles 12. The heat sealing apparatus 214 includes a heated platen 216 that applies heat and pressure against each lid 200 for a predetermined length of time, to form a seal between the lid 200 and the bottle 12. The heated platen 216 is in a two by six configuration to seal twelve of the bottles 12 at a time.

At station 37, the lid 200 seal and bottle 12 integrity are checked in a known manner by a seal integrity apparatus (not shown) comprising, for example, a bottle squeezing mechanism and a proximity sensor. Each bottle 12 is squeezed by the bottle squeezing mechanism which causes the lid 200 on the bottle 12 to extend upward. The proximity sensor detects if the lid 200 has extended upward, which indicates an acceptable seal, or whether the seal remains flat, which indicates a leaking seal or bottle 12. The location of the defective bottles 12 are recorded by the control system 550 so that the defective bottles will not be packed.

Bottle discharge from the sterilization tunnel 90 of the filler apparatus 50 occurs at stations 38 and 40 as illustrated in FIGS. 3, 13 and 14. A bottle discharge apparatus 280 is located at stations 38 and 40. At this point in the filler apparatus 50, the filled and sealed bottles 12 are forced in an upward direction such that a top portion 284 of each bottle 12 protrudes through the opening 282 in the sterilization tunnel 90 (FIG. 14). A rotating cam 290 or other suitable means (e.g., an inflatable diaphragm, etc.) may be used to apply a force against the bottom 120 of each bottle 12 to force the bottle 12 in an upward direction.

As illustrated in FIG. 14, the bottle discharge apparatus 280 comprises a lifting apparatus 286 that includes a gripper 288 that grasps the top portion 284 of each bottle 12 and lifts the bottle 12 out through the opening 282 in the sterilization tunnel 90. In order to ensure that contaminated air cannot enter the sterilization tunnel 90, the sterile air in the sterilization tunnel 90 is maintained at a higher pressure than the air outside the sterilization tunnel 90. Thus, sterile air is always flowing out of the sterilization tunnel 90 through the opening 282. In addition, the gripper 288 never enters the sterilization tunnel 90, because the top portion 284 of the bottle 12 is first lifted out of the sterilization tunnel 90 by the action of the rotating cam 290 before being grabbed by the gripper 288.

FIG. 15 illustrates a top view of the filler apparatus 50 including the bottle infeed and sterilization apparatus 60, the interior bottle sterilization apparatus 116, and the activation and drying apparatus 152. FIG. 15 additionally illustrates the main filler apparatus 160, the lid sterilization and heat sealing apparatus 162, and the bottle discharge apparatus 280.

Referring again to FIGS. 1 and 14, the lifting apparatus 286 lifts the bottles 12 at station 38 and places the bottles 12 in a first lane 292 that transports the bottles 12 to a first capping apparatus 410. In addition, the lifting apparatus 286 lifts the bottles 12 at station 40 and places the bottles 12 in a second lane 294 that transports the bottles 12 to a second capping apparatus 400.

The first capping apparatus 410 secures a cap (not shown) on the top of each bottle 12 in the first lane 292. The second capping apparatus 400 secures a cap on the top of each bottle 12 in the second lane 294. The caps are secured to the bottles 12 in a manner known in the art. It should be noted that the capping process may be performed outside of the sterilization tunnel 90 because each of the bottles 12 have previously been sealed within the sterilization tunnel 90 by the lid sterilization and heat sealing apparatus 162 using a sterile lid 200.

After capping, the bottles 12 are transported via the first and second lanes 292, 294 to labelers 460 and 470. The first labeling apparatus 470 applies a label to each bottle 12 in the first lane 292. The second labeling apparatus 460 applies a label to each bottle 12 in the second lane 294.

From the first labeling apparatus 470, the bottles 12 are transported along a first set of multiple lanes (e.g., 4) to a first case packing apparatus 490. From the second labeling apparatus 460, the bottles 12 are transported along a second set of multiple lanes to a second case packing apparatus 480. Each case packing apparatus 480, 490 gathers and packs a plurality of the bottles 12 (e.g., twelve) in each case in a suitable (e.g., three by four) matrix.

A first conveyor 296 transports the cases output by the first case packer 490 to a first palletizer 510. A second conveyor 298 transports the cases output by the second case packer 480 to a second palletizer 500. A vehicle, such as a fork lift truck, then transports the pallets loaded with the cases of bottles 12 to a storage warehouse.

Referring again to FIG. 3, the main conveyor 106 and each conveying plate 94 are cleaned and sanitized once during each revolution of the main conveyor 106. Specifically, after each empty conveying plate 94 passes around the pulley 108, the conveying plate 94 is passed through a liquid sanitizing apparatus 300 and a drying apparatus 302. The liquid sanitizing apparatus 300 sprays a mixture of a sterilizing agent (e.g., oxonia, (hydrogen peroxide and peroxyacetic acid)) over the entire surface of each conveying plate 94 and associated components of the main conveyor 106. In the drying apparatus 302, heated air with is used to dry the main conveyor 106 and conveying plates 94.

Stations 1 through 40 are enclosed in the sterilization tunnel 90. The sterilization tunnel 90 is supplied with air that is pressurized and sterilized. The interior of the sterilization tunnel 90 is maintained at a pressure higher than the outside environment in order to eliminate contamination during the bottle processing. In addition, to further ensure a sterile environment within the sterilization tunnel 90, the sterile air supply provides a predetermined number of air changes (e.g., 2.5 changes of air per minute) in the sterilization tunnel 90.

Before bottle production is initiated, the bottle infeed and sterilization apparatus 60 and the filler apparatus 50 are preferably sterilized with an aseptic sterilant. For example, a sterilant such as a hot hydrogen peroxide mist may be applied to all interior surfaces of the bottle infeed and sterilization apparatus 60 and the filler apparatus 50. Then, hot sterile air is supplied to activate and remove the hydrogen peroxide, and to dry the interior surfaces of the bottle infeed and sterilization apparatus 60 and the filler apparatus 50.

Figure 16:
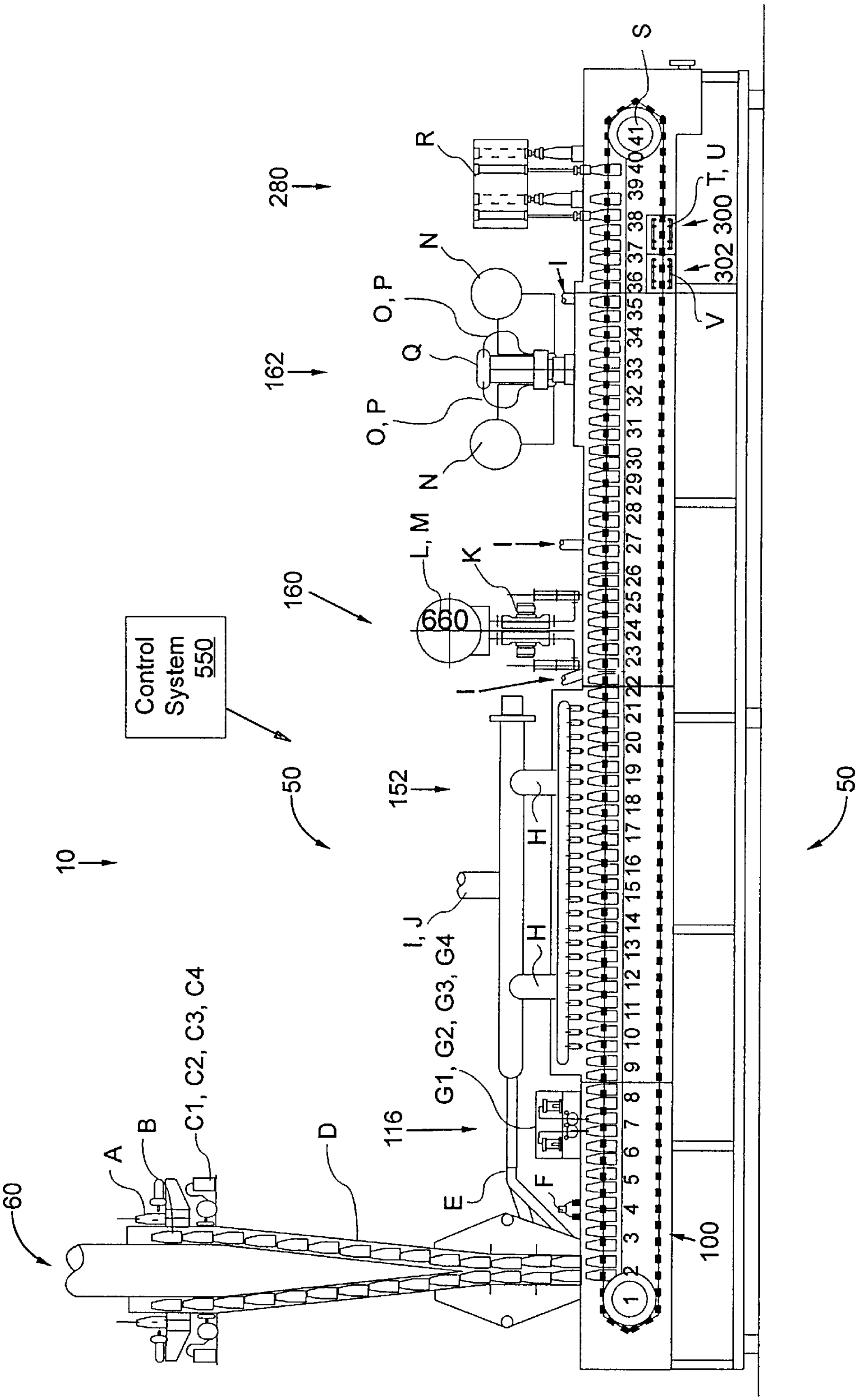
FIG. 16 is a side view of the aseptic processing apparatus indicating the control and monitoring locations that are interfaced with a control system.

FIG. 16 is a side view of the aseptic processing apparatus 10 of the present invention indicating the location of the control and monitoring devices that are interfaced with the control system 550. The control system 550 gathers information and controls process functions in the aseptic processing apparatus 10. A preferred arrangement of the control and monitoring devices are indicated by encircled letters in FIG. 16. A functional description of each of the control and monitoring devices is listed below. It should be noted that these control and monitoring devices are only representative of the types of devices that may be used in the aseptic processing apparatus 10 of the present invention. Other types and combinations of control and monitoring devices may be used without departing from the intended scope of the present invention. Further, control system 550 may respond in different ways to the outputs of the control and monitoring devices. For example, the control system 550 may automatically adjust the operational parameters of the various components of the aseptic processing apparatus 10, may generate and/or log error messages, or may even shut down the entire aseptic processing apparatus 10. In the preferred embodiment of the present invention, the control and monitoring devices include:

A. A bottle counter to ensure that a predetermined number of the bottles 12 (e.g., six bottles) on each upper horizontal row 24, 28 enter the loading area of the bottle infeed and sterilization apparatus 60.

B. A proximity sensor to ensure that the first group of bottles 12 has dropped into the first bottle position in the bottle infeed and sterilization apparatus 60.

C1. A conductivity sensor to ensure that the measuring cup used by the sterilant application apparatus 36 is full.

C2. A conductivity sensor to ensure that the measuring cup used by the sterilant application apparatus 36 is emptied in a predetermined time.

C3. A pressure sensor to ensure that the pressure of the air used by the sterilant application apparatus 36 is within predetermined atomization requirements.

C4. A temperature sensor to ensure that each heat heating element used by the sterilant application apparatus 36 is heated to the correct temperature.

D. A proximity sensor (e.g., proximity sensor 71, FIG. 3) to ensure that a bottle jam has not occurred within the bottle infeed and sterilization apparatus 60.

E. A temperature sensor to ensure that the temperature of the heated sterile air entering the bottle infeed and sterilization apparatus 60 is correct.

F. A proximity sensor that to ensure that each conveying plate 94 is fully loaded with bottles 12.

G1. A conductivity sensor to ensure that the measuring cup used by the interior bottle sterilization apparatus 116 is full.

G2. A conductivity sensor to ensure that the measuring cup used by the interior bottle sterilization apparatus 116 is emptied in a predetermined time.

G3. A pressure sensor to ensure that the pressure of the air used by the interior bottle sterilization apparatus 116 is within predetermined atomization requirements.

G4. A temperature sensor to ensure that each heat heating element used by the interior bottle sterilization apparatus 116 is heated to the correct temperature.

H. A temperature sensor to ensure that the air drying temperature within the activation and drying apparatus 152 is correct.

I. A plurality of flow sensors to ensure that the airflow rate of the sterile air entering the sterilization tunnel 90 is correct.

J. A pressure sensor to ensure that the pressure of the sterile air entering the activation and drying apparatus 152 is correct.

K. A measuring device (e.g., volumetric measuring device 188, FIG. 3) to ensure that each bottle 12 is filled to a predetermined level.

L. A pressure sensor to ensure that the pressure in the product tank 182 is above a predetermined level.

M. A level sensor to ensure that the level of product in the product tank 182 is maintained at a predetermined level.

N. Proximity sensors to ensure that the daisy chains 202 of lids 200 are present in the lid sterilization and heat sealing apparatus 162

O. A level sensor to ensure that the hydrogen peroxide level in the hydrogen peroxide bath 204 in the lid sterilization and heat sealing apparatus 162 is above a predetermined level.

P. A temperature sensor to ensure that the temperature of the hot sterile air knives 208 of the lid sterilization and heat sealing apparatus 162 is correct.

Q. A temperature sensor to ensure that the heat sealing apparatus 214 is operating at the correct temperature.

R. Proximity sensors to ensure that the bottles 12 are discharged from the filler.

S. A speed sensor to measure the speed of the conveying apparatus 100.

T. A concentration sensor to ensure that the concentration of oxonia is maintained at a predetermined level in the sanitizing apparatus 300.

U. A pressure sensor to ensure that the pressure of the oxonia is maintained above a predetermined level in the sanitizing apparatus 300.

V. A temperature sensor to ensure that the drying temperature of the drying apparatus 302 is correct.

The following steps are performed during the "Clean In Place" (CIP) process in the filler apparatus 50;

23. Conductivity sensor to verify caustic and acid concentrations.

24. Temperature sensor to verify "Clean In Place" solution temperatures.

25. Flow meter to verify "Clean In Place" flow rates.

26. Time is monitored to ensure that adequate cleaning time is maintained.

The follow steps are performed during sterilization of the bottle filler apparatus 50;

27. Temperature sensors for measuring steam temperatures.

28. Proximity sensors to ensure filler nozzle cleaning/sterilization cups are in position.

29. Temperature sensors for air heating and cooling.

30. Flow meter for hydrogen peroxide injection.

31. Time is monitored to ensure the minimum time periods are met (steam, hydrogen peroxide application and activation/drying).

The foregoing description of the present invention has been presented for purposes of illustration and description. It is not intended to be exhaustive or to limit the invention to the precise form disclosed, and many modifications and variations are possible in light of the above teaching. Such modifications and variations that may be apparent to a person skilled in the art are intended to be included within the scope of this invention.

I claim:

1. Apparatus comprising:

a sterilization tunnel for surrounding a plurality of containers with pressurized gas; and a plurality of zones within the sterilization tunnel having different sterilant concentration levels therein wherein the sterilant concentration levels in the plurality of zones are maintained at a ratio of at least about 5 to 1.

2. The apparatus of claim 1, wherein said plurality of zones have different gas flow rates.

3. The apparatus of claim 1, wherein the sterilant concentration levels of the plurality of sterilant concentration zones are maintained at a ratio of at least about 1,000 ppm to 0.1 ppm.

4. Apparatus comprising:

a sterilization tunnel for surrounding a plurality of containers with pressurized gas;

a sterilant supply source to supply sterilant into the sterilization tunnel;

a control system, operatively attached to a plurality of sterilant concentration zones within the sterilization tunnel, for automatically adjusting the operational parameters of the tunnel, wherein the sterilant concentration levels in the plurality of sterilant concentration zones are maintained at a ratio of at least about 5 to 1;

at least one gas supply source to supply the pressurized gas into the sterilization tunnel; and at least one gas exit to allow the pressurized gas to escape the sterilization tunnel.

5. The apparatus of claim 3, further comprising at least one partition forming the plurality of sterilant concentration zones within the sterilization tunnel.

6. The apparatus of claim 3, wherein the gas is sterile air.

7. The apparatus of claim 3, wherein the sterilant is hydrogen peroxide.

8. The apparatus of claim 3, further including a product filler and a lidding apparatus opening into a sterile zone of the sterilization tunnel.

9. The apparatus of claim 8, wherein the concentration of the sterilant hydrogen peroxide is less than 0.5 ppm in the sterile zone.

10. The apparatus of claim 3, further including an interior bottle sterilization apparatus opening into a sterile zone of the sterilization tunnel.

11. The apparatus of claim 10, wherein the concentration of the sterilant hydrogen peroxide is about 1000 ppm in the sterile zone.

12. The apparatus of claim 3, further including an activation and drying apparatus opening into the sterilization tunnel.

13. The apparatus of claim 12, wherein the concentration of the sterilant hydrogen peroxide is about 3 ppm.

14. The apparatus of claim 3, further including a bottle discharge apparatus opening into the sterilization tunnel.

15. The apparatus of claim 14, wherein the concentration of the sterilant hydrogen peroxide is about 0.1 ppm.

16. The apparatus of claim 3, wherein the containers are bottles.

17. Apparatus comprising:

a sterilization tunnel for surrounding a plurality of containers with pressurized gas;

a sterilant supply source to supply sterilant into the sterilization tunnel;

a plurality of zones having a plurality of gas nozzles within the sterilization tunnel;

at least one partition forming a plurality of sterilant concentration zones within the sterilization tunnel wherein the sterilant concentration levels of the plurality of sterilant concentration zones are maintained at a ratio of at least about 5 to 1;

at least one gas supply source to supply the pressurized gas into the sterilization tunnel; and at least one gas exit to allow the pressurized gas to escape the sterilization tunnel.

18. The apparatus of claim 17, further including at least one partition forming gas flow zones.

19. The apparatus of claim 18, wherein each partition comprises openings for allowing objects to pass through each partition.

20. The apparatus of claim 17, wherein the pressurized gas is sterile air.

21. The apparatus of claim 17, wherein the sterilant is hydrogen peroxide.

22. The apparatus of claim 17, further including an activation and drying apparatus opening into a first of said gas flow zones.

23. The apparatus of claim 22, wherein sterile air enters the first gas flow zone at a rate of about 2400 cfm.

24. The apparatus of claim 23, wherein sterile air exits the first gas flow zone at a rate of about 1500 cfm.

25. The apparatus of claim 17, further including a product filler and a lidding apparatus opening into a second of said gas flow zones of the sterilization apparatus.

26. The apparatus of claim 25, wherein sterile air enters the second gas flow zone at a rate of about 1000 cfm.

27. The apparatus of claim 17, further including a bottle discharge apparatus opening into a third of said gas flow zones of the sterilization tunnel.

28. The apparatus of claim 27, wherein sterile air exits the third gas flow zone at a rate of about 100 cfm.

29. The apparatus of claim 17, further including a bottle infeed and sterilization apparatus with an opening into a fourth gas flow zone of the sterilization tunnel.

30. The apparatus of claim 29, wherein sterile air enters the infeed and sterilization apparatus at a rate of about 1800 cfm.

31. The apparatus of claim 29, wherein sterile air from the infeed and sterilization apparatus together with the fourth gas flow zone exits the infeed and sterilization apparatus at a rate of about 3600 cfm.

32. The apparatus of claim 17, wherein the containers are bottles.

33. A method comprising:

providing a sterilization tunnel for surrounding a plurality of containers with pressurized gas;

introducing sterilant from a sterilant supply source into the sterilization tunnel;

providing a plurality of sterilant concentration zones within the sterilization tunnel wherein the sterilant concentration levels of the plurality of sterilant concentration zones are maintained at a ratio of at least about 5 to 1;

providing at least one partition for forming said sterilant concentration zones;

setting the level of sterilant concentration by a control system;

introducing pressurized gas from at least one gas supply source into the sterilization tunnel; and allowing the pressurized gas to escape the sterilization tunnel.

34. The method of claim 33, further comprising providing a control system operatively attached to the plurality of sterilant concentration zones within the sterilization tunnel.

35. The method of claim 33, wherein the step of introducing gas further comprises introducing sterile air.

36. The method of claim 33, wherein the sterilant is hydrogen peroxide.

37. Apparatus comprising:

means for providing a plurality of containers in a sterilization tunnel;

means for providing a plurality of sterilant concentration zones within the sterilization tunnel wherein the sterilant concentration levels of the plurality of sterilant concentration zones are maintained at a ratio of at least about 5 to 1; and means for providing a plurality of gas flow rates within the sterilization tunnel.

* * * * *